(12) United States Patent
Battyani et al.

(10) Patent No.: US 10,267,932 B2
(45) Date of Patent: Apr. 23, 2019

(54) METHOD AND APPARATUS FOR X-RAY DETECTION SYSTEM GAIN CALIBRATION USING A PULSER

(71) Applicants: Marc Battyani, Arlington, MA (US); Peter Hardman, Woburn, MA (US)

(72) Inventors: Marc Battyani, Arlington, MA (US); Peter Hardman, Woburn, MA (US)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 42 days.

(21) Appl. No.: 15/017,215

(22) Filed: Feb. 5, 2016

(65) Prior Publication Data

US 2017/0227661 A1    Aug. 10, 2017

(51) Int. Cl.
*G01T 7/00* (2006.01)
*G01N 23/223* (2006.01)

(52) U.S. Cl.
CPC ........... *G01T 7/005* (2013.01); *G01N 23/223* (2013.01); *G01N 2223/303* (2013.01)

(58) Field of Classification Search
CPC . G01T 7/005; G01N 23/223; G01N 2223/303
See application file for complete search history.

(56) References Cited

U.S. PATENT DOCUMENTS

| 4,068,306 A * | 1/1978 | Chen | A61B 6/032 341/120 |
|---|---|---|---|
| 4,070,707 A * | 1/1978 | Barber | A61B 6/032 341/118 |
| 5,206,174 A * | 4/1993 | Gehrke | G01T 1/36 250/253 |
| 2003/0183771 A1 * | 10/2003 | Hirai | H04N 5/32 250/370.09 |
| 2012/0127356 A1 * | 5/2012 | Matsuura | H04N 5/3577 348/313 |
| 2014/0254746 A1 * | 9/2014 | Kodaira | A61B 6/03 378/4 |

* cited by examiner

*Primary Examiner* — Christine S. Kim
(74) *Attorney, Agent, or Firm* — C. Tricia Liu

(57) ABSTRACT

Disclosed are circuits for automatic calibration of the gain of electronic amplification and digitization systems for use with X-ray detectors. The calibration is based on injecting predetermined pulses into the electronic system and deriving a calibration ratio based the digital value of their amplitude with the digital value of the same pulses, unamplified and digitized with a high accuracy reference ADC. All ADCs, as well as the DACs used to control the pulser amplitude are referenced to a single common reference voltage. Calibration for non-linearity of the gain is disclosed with an alternative embodiment for the same circuits.

18 Claims, 10 Drawing Sheets

METHOD AND APPARATUS FOR X-RAY DETECTION SYSTEM GAIN CALIBRATION USING A PULSER

FIELD OF THE INVENTION

The present invention relates to X-ray analyzers for detecting X-rays and generating corresponding response electronic signals, and more particularly to improved signal processing circuits which enhance stability and accuracy of the energy scale of the X-ray spectra by using a pulser.

BACKGROUND OF THE INVENTION

An X-ray analyzer, such as an X-ray fluorescence (XRF) or X-ray diffraction (XRD) instrument generally comprises an X-ray source, an X-ray detector and associated electronics. The X-ray detector is usually energy dispersive, with each incident X-ray producing an electronic signal whose charge is proportional to the energy of the X-ray. The detector electronics is designed to amplify each signal so that it becomes large enough to accurately measure the charge corresponding to the X-ray energy. The amplified signals are subsequently digitized and the digital values are used to construct an X-ray spectrum. Provided the gain of the entire electronic amplification and digitization system remains constant, the digital value of the amplified pulse is proportional to the energy of the associated X-ray, and with suitable calibration the X-ray energy can be determined. Knowing the energy of each X-ray, the signals from multiple X-rays striking the detector can be converted into a spectrum, which is a plot of X-ray energies vs the number of X-rays received with that energy. Such a spectrum exhibits peaks at energies which correspond to the characteristic X-ray energies of elements within the sample being measured. The position, magnitude and width of the peaks are critical parameters enabling identification of the elements in the sample and determination of their concentration.

In order to ensure that test results are accurate and repeatable, it is important to avoid electronic drift of signals from the detector. Signal drift results in X-rays of the same energy being assigned a different energy in the spectrum at different measurement times. The signal drift may cause misidentification of elements and/or errors in measurement of their concentration.

Drift of the gain of the electronic amplification and digitization system is a major source of signal drift. The drift may be due to instability of any of the components of the electronic system. For example, it is well known that the properties of electronic components are sensitive to temperature, and this temperature sensitivity can be particularly important for a compact, hand-held XRF instrument whose temperature may rise significantly from a cold start during the course of a long measurement or series of measurements. The temperature change results in variable electronic gain which causes drift in the energy scale of measured X-ray spectra. Energy scale drift includes drift during a single measurement, drift of the energy scale between different measurements on the same instrument, and inconsistent measurements of the same or similar sample made on different instruments.

One solution to the problem of energy scale drift in existing practice is to perform frequent manual calibrations. Energy scale calibration may be achieved by exposing the X-ray detector to X-rays of known energy, either using X-rays emitted from a radioactive source, or using secondary X-rays emitted from a known target material. In one example from existing practice, the energy scale is re-calibrated every few hours using Fe and Mo characteristic X-rays from a stainless steel sample containing both elements. However, irrespective of the calibration method used in existing practice, useful operation of the X-ray instrument must be interrupted, which is inconvenient and is therefore often neglected by operators. In the case of a handheld instrument, the instrument must usually be manually inserted into a docking station containing a known target material. The known energy of X-ray peaks from the target is compared with the measured energy in order to calibrate the gain. Since frequent manual calibration is inconvenient, the time between successive calibrations can be many hours, during which time significant temperature change and consequent energy drift may occur, causing degradation of the XRF measurement accuracy.

There is therefore a need in existing practice for a calibration method which is automatic and fast, causing minimal or no interruption to normal operation of the measuring device. The calibration method should be programmable to occur either after each measurement or continuously during the course of all measurements. In addition, the calibration method should encompass the entire electronic amplification and digitization system.

Another problem in existing practice is that the determination of X-ray energy in the amplified and digitized signal is subject to non-linearity in the amplification and digitization components. The primary effect of non-linearity is that the system gain varies with the amplitude of the signal. This problem is especially severe when, as is usually the case, a charge-sensitive pre-amplifier is used as part of the amplification of detector signals. A charge-sensitive amplifier has the property that its output voltage rises approximately as a step-function in response to input of the charge from an incident X-ray. The output voltage continues to rise to higher and higher voltage levels in response to subsequent X-ray signals, with the height of each voltage step being proportional to the energy of the corresponding X-ray. The output voltage continues to rise until an upper voltage threshold is reached and an external reset signal is applied to return the output voltage to zero or a lower voltage threshold. The problem with non-linearity arises because an X-ray of given energy may arrive when the pre-amplifier output voltage is at any level between the lower and upper thresholds, and non-linearity of the subsequent amplification and digitization system causes different energy to be assigned to the X-ray depending on where the pre-amplifier voltage happened to be at its time of arrival.

The effects of non-linearity in detector amplification and digitization have not been addressed in existing practice even though commercially available X-ray detectors may often incorporate a charge-sensitive preamplifier within the detector enclosure to minimize signal noise. The non-linearity effects generally have weak dependence on temperature, so that there is no significant drift of the non-linear response. A one-time calibration of a particular instrument may be sufficient to compensate for the non-linear effects. However, an efficient method of conducting a calibration to compensate for the non-linear effects is lacking in the existing market.

SUMMARY OF THE INVENTION

The purpose of the invention is to alleviate problems with existing practice, particularly with respect to the inaccuracy and drift in the detector energy scale calibration. This purpose is achieved by frequent calibration of the energy scale with a novelly applied calibration pulse signal which is injected into the same electronic amplification and digitization system as the detector signals. In order to enhance the stability of the calibration, a single common reference voltage is used for all the digitization elements and for setting the amplitude of the calibration pulse signals. Calibration of non-linearity of the electronic amplification and digitization system is achieved with a one-time calibration of each instrument.

One embodiment of the invention is a circuit for sequential injection of signal pulses and calibration pulses into the electronic amplification and digitization system. The circuit comprises a detector, one or more amplifiers, a pulser, a switch for sequentially injecting detector signal pulses and calibration pulses into the amplifiers, a reference analog-to-digital converter (ADC), a processing ADC, and a common reference voltage for the reference ADC, the processing ADC and the pulser.

A second embodiment of the invention is a circuit for simultaneous injection of signal pulses and calibration pulses into the electronic amplification and digitization system. The circuit comprises a detector, one or more amplifiers, a pulser, a reference ADC, a processing ADC, a pulse discriminator, and a common reference voltage for the reference ADC, the processing ADC and the pulser.

A third embodiment of the invention is a circuit and method for using calibration pulses with varying base voltage to perform a one-time calibration of the non-linear behavior of the electronic amplification and digitization system. The circuit comprises one or more amplifiers, a pulser comprising two digital-to-analog converters (DACs) and a pulser switch, a reference ADC, a processing ADC, and a common reference voltage for the reference ADC, the processing ADC and both pulser DACs.

DETAILED DESCRIPTION OF PREFERRED EMBODIMENTS

Note that in the description below, the term "voltage" is used to designate analog signals, and the term "value" is used to designate digital quantities. Note also that in the description and the drawings a symbol without angle brackets is used to denote an analog quantity, and a symbol with angle brackets is used to denote a digital quantity. For example, the analog voltage of a calibration pulse is P, and its digitized equivalent is <P>.

Figure 1:
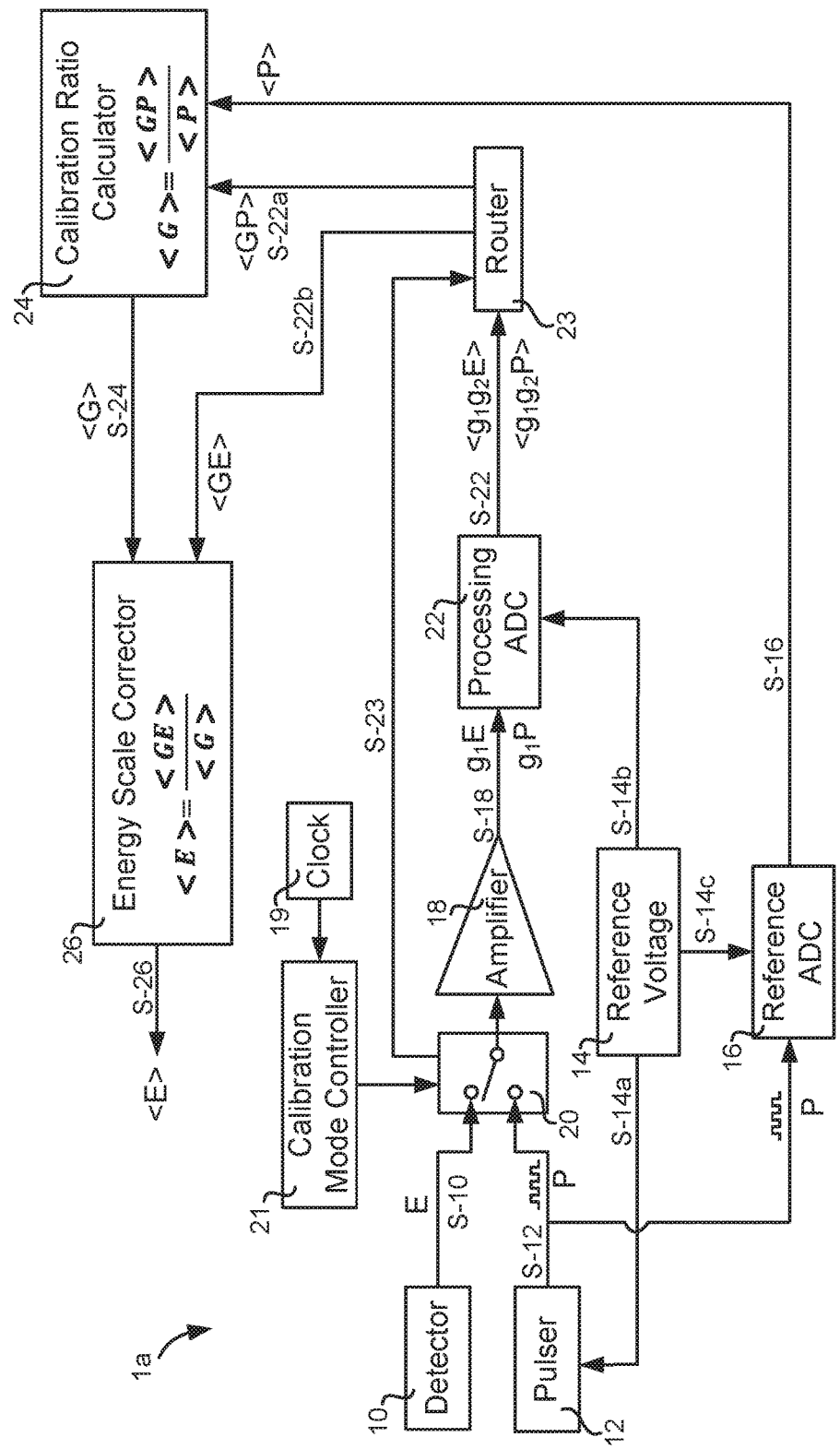
FIG. 1 is a schematic of a detector signal processing circuit with sequential calibration pulse injection according to the present disclosure.

FIG. 1 is a schematic illustration of a detector signal processing circuit 1a with sequential calibration pulse injection. Circuit 1a includes a detector 10 which produces a detector response signal S-10 representative of an energy E of an incident X-ray. In an embodiment herein presented, detector 10 includes a charge-sensitive pre-amplifier (not shown) which may be incorporated within the enclosure of detector 10, and response signal S-10 consists of a step in output voltage whose height is indicative of energy E. Circuit 1a also includes a pulser 12 which produces a calibration pulse signal S-12 with a pulse amplitude P, and a switch 20. Optionally, the position of switch 20 is controlled by a calibration mode controller 21 receiving timing information from a clock 19. Calibration mode controller 21 may set switch 20 either to an operating mode in which detector response signal S-10 is input into an amplifier 18, or to a calibration mode in which calibration pulse signal S-12 is input into amplifier 18. It is to be understood that amplifier 18 may represent one or more signal amplification elements, including one or more pre-amplifiers, amplifiers or other amplification devices. Amplifier 18, having a gain $g_1$, produces an amplified voltage S-18, which is equal to an amplified response signal voltage $g_1E$ when switch 20 selects detector response signal S-10, and is equal to an amplified pulse voltage $g_1P$ when switch 20 selects calibration pulse signal S-12. In practice, gain $g_1$ is not constant, but is a variable which may drift depending on the temperature of internal amplifier components, such as resistors.

Amplified voltage S-18 is input into a processing analog-to-digital converter (ADC) 22, which is a fast ADC capable of digitizing at high data rates. Ideally the gain of processing ADC 22 should be unity, meaning that its output should be the exact digital equivalent of its analog input. In practice, however, the gain of any ADC is a variable which may change depending on various factors including the value of the reference voltage and the temperature of the ADC components. In particular, a fast ADC such as processing ADC 22 is typically available only with relatively low resolution, such as 16 bits in an exemplary embodiment. The specification for gain drift for such an ADC may be as large as 30-50 ppm. Therefore, to ensure accuracy and reproducibility of the energy scale derived by circuit 1a, it is essential that the calibration procedure should take account of any drift in the gain of processing ADC 22. If a gain of processing ADC 22 is $g_2$, then the digitized output from processing ADC 22 is an amplified voltage value S-22, whose value depends on the product of the gain $g_1$ of amplifier 18 and the gain $g_2$ of processing ADC 22.

The value of amplified voltage value S-22 also depends on the position of switch 20. When switch 20 selects detector response signal S-10, amplified voltage value S-22 is equal to a response signal voltage value $<g_1g_2E>$. When switch 20 selects calibration pulse signal S-12, amplified voltage value S-22 is equal to a pulse voltage value $\langle g_1g_2P\rangle$. The quantity $g_1g_2$ is hereinafter referred to as an overall gain G, where $G=g_1g_2$ is the overall gain of the electronic system including both the amplification and the digitization components.

Circuit 1a further includes a router 23 which is in communication with switch 20 via a signal S-23. Router 23 is thereby able to route amplified voltage value S-22 to an amplified calibration voltage value S-22a when switch 20 selects calibration pulse signal S-12, and to route amplified voltage value S-22 to an amplified operating voltage value S-22b when switch 20 selects detector response signal S-10. Amplified calibration voltage value S-22a is equal to $\langle GP\rangle$, and amplified operating voltage value S-22b is equal to $\langle GE\rangle$.

Calibration pulse signal S-12 is also input into a reference ADC 16 which outputs a digital reference pulse value S-16. Digital reference pulse value S-16 is equal to $\langle P\rangle$, which is a digitized value of pulse amplitude P. Reference ADC 16 does not need to be a fast ADC because it needs only to digitize reference pulses at relatively low rate. Therefore reference ADC 16 is chosen to be a high resolution ADC with superior drift specifications. In an embodiment, reference ADC 16 has 24 bit resolution and drift specification of less than 2 ppm.

It should be noted that the amplitude of the pulses from pulser 12 is preferably chosen so that the pulse amplitude is approximately the same as an average detector response signal S-10. The frequency of pulses from pulser 12 is preferably chosen so that the pulse arrival time in calibration mode is approximately the same as the average arrival time of detector response signals S-10 in operating mode. These conditions of pulse amplitude and frequency are chosen so that the calibration pulses most accurately mimic the gain and linearity performance of the overall electronic system including both the amplification and the digitization components.

Circuit 1a also includes a single common reference voltage element 14, which serves as the voltage reference for pulser 12 via a signal S-14a, as well as the reference for processing ADC 22 via a signal S-14b and for reference ADC 16 via a signal S-14c.

It should be noted that one of the novel aspects of the design of circuit 1a is that connections S-14a, S-14b and S-14c all share the same signal, which is reference voltage 14.

Circuit 1a further includes a calibration ratio calculator 24 providing a value of a calibration ratio. Digital reference pulse value S-16 and amplified calibration voltage value S-22a are used to calculate the calibration ratio, which is equal to amplified calibration voltage value S-22a (equal to $\langle GP\rangle$) divided by digital reference pulse value S-16 (equal to $\langle P\rangle$). The calibration ratio may be calculated for many pulses during a calibration time, and an average value obtained. The result from calibration ratio calculator 24 is a gain value S-24, which is equal to a digital representation $\langle G\rangle$ of overall gain G.

$$\langle G\rangle = \frac{\langle GP\rangle}{\langle P\rangle} \qquad (1)$$

where $\langle GP\rangle$ and $\langle P\rangle$ are averaged over the calibration time.

It should be noted that an important novel aspect of the present invention is the use of calibration ratio calculator 24 to calculate overall gain G of the entire electronic system including both amplification and digitization components.

The calculation is based on comparison of digitized calibration pulses from pulser 12 obtained by two different electronic routes. The first route is by digitization of calibration pulse signal S-12 using reference ADC 16 without any amplification. The second route is when switch 20 selects calibration pulse signal S-12, and the calibration pulses are amplified by amplifier 18 and then digitized by processing ADC 22. Importantly, processing ADC 22 and reference ADC 16 use the same reference voltage 14, so that any drift in the reference voltage causes the same gain drift in both processing ADC 22 and reference ADC 16, and the drift cancels out by division done by calibration ratio calculator 24. Moreover, reference ADC 16 has much greater accuracy and much lower drift than processing ADC 22, so that its output may be used as a calibration reference for the gain of the overall electronic system.

It should also be noted that the calculation done by calibration ratio calculator 24 may be made any time switch 20 is set to select calibration pulse signal S-12. Calibration time may be any chosen value, which may be as short as 100 msec, and therefore calibration may be performed frequently with minimal interruption of useful operation of the X-ray instrument.

During instrument measurement operation, when switch 20 is set to select detector response signal S-10, both gain value S-24 and amplified operating voltage value S-22b are used by an energy scale corrector 26 to calculate a corrected energy value S-26. Corrected energy value S-26 is equal to amplified operating voltage value S-22b (equal to $\langle GE\rangle$) divided by gain value S-24 (equal to $\langle G\rangle$). The result of this calculation is corrected energy value S-26, which is a corrected digital representation $\langle E\rangle$ of detector response signal S-10.

$$\langle E\rangle = \frac{\langle GE\rangle}{\langle G\rangle} \qquad (2)$$

Corrected energy value S-26 is calculated for each detector signal, corresponding to each incident X-ray, and is used to construct an energy spectrum, which is a plot of X-ray energy vs number of X-rays incident on the detector with that energy. Corrected energy value S-26 is a calibrated energy value which takes account of substantially all drift in the amplification and digitization electronics, and the calibration may be performed as frequently as desired by programming the operation of switch 20 using calibration mode controller 21. Operation of switch 20 can also be initiated manually by an operator actuating a button or virtual button, (not shown in FIG. 1), whenever a need for calibration is deemed fit.

Figure 2:
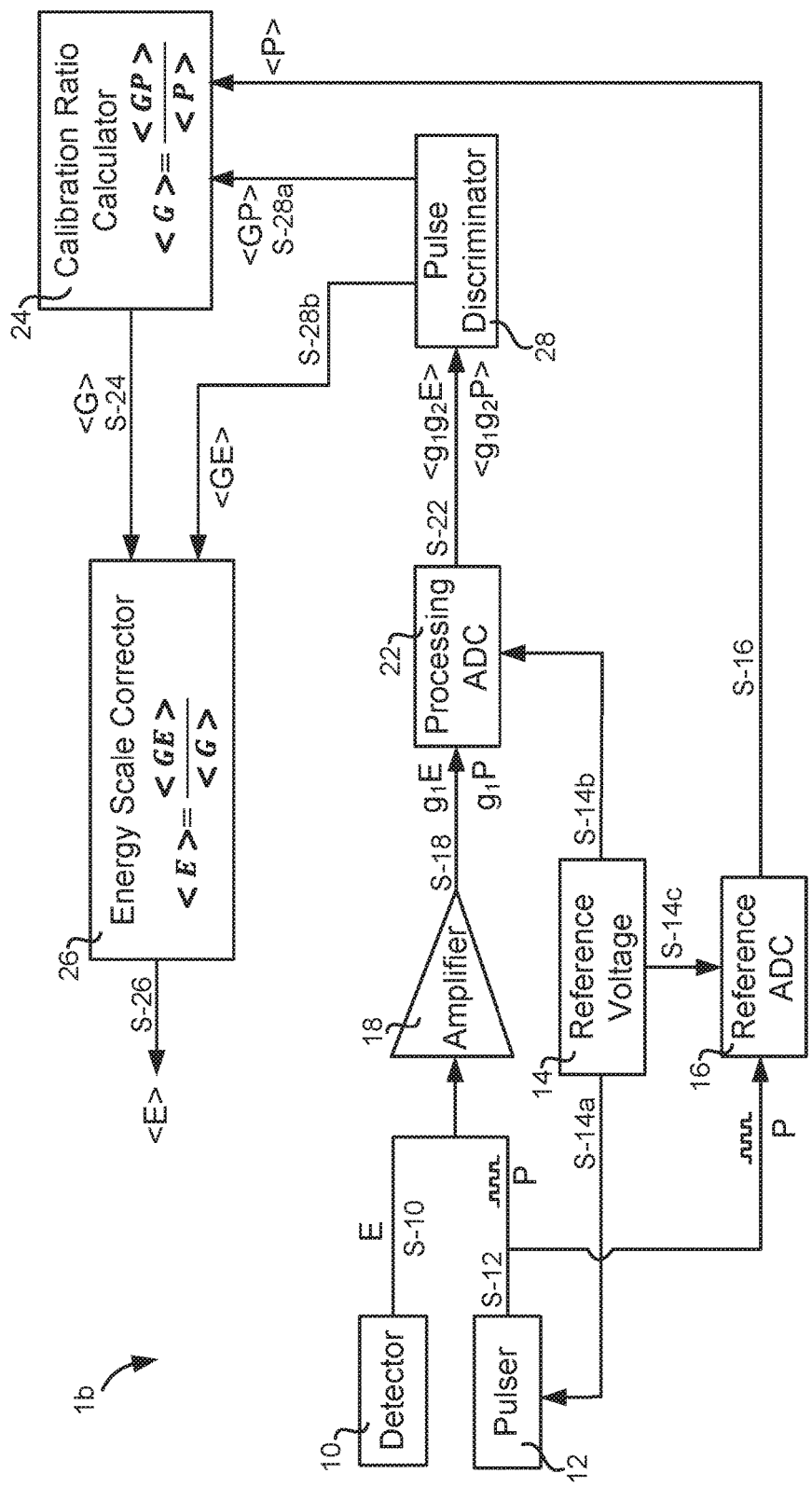
FIG. 2 is a schematic of a detector signal processing circuit with simultaneous calibration pulse injection according to the present disclosure.

FIG. 2 is a schematic illustration of an alternative detector signal processing circuit 1b with simultaneous calibration pulse injection. Circuit 1b includes components equivalent to those in circuit 1a shown in FIG. 1, with two notable exceptions. The first difference between circuits 1a and 1b is that switch 20 is absent in circuit 1b. The second difference is that router 23 in circuit 1a is replaced with a pulse discriminator 28 in circuit 1b.

In circuit 1b, detector response signal S-10 and calibration pulse signal S-12 are both injected simultaneously and continuously into amplifier 18. Amplified voltage S-18 therefore comprises a mixture of both amplified response signal voltage $g_1E$ and amplified pulse voltage $g_1P$. Similarly, amplified voltage value S-22 comprises a mixture of response signal voltage value $\langle g_1g_2E\rangle$ and pulse voltage value $<g_1 g_2 P>$. Amplified voltage value S-22 is input into a pulse discriminator 28 whose function is to separate the response signal and pulse voltage values contained within amplified voltage value S-22. Pulse voltage values are separated to a discriminated calibration value S-28a, and detector response signal values are separated to a discriminated response value S-28b. The method of operation of pulse discriminator 28 is described below in connection with FIG. 3. Subsequent operation of circuit 1b is the same as operation of circuit 1a, namely calibration ratio calculator 24 provides calibration ratio S-24 used for the calculation of corrected energy value S-26. However it should be noted that, in the case of circuit 1b, calibration occurs continuously throughout every measurement operation, with no interruption or slowdown of the measurement operation.

Figure 3A:
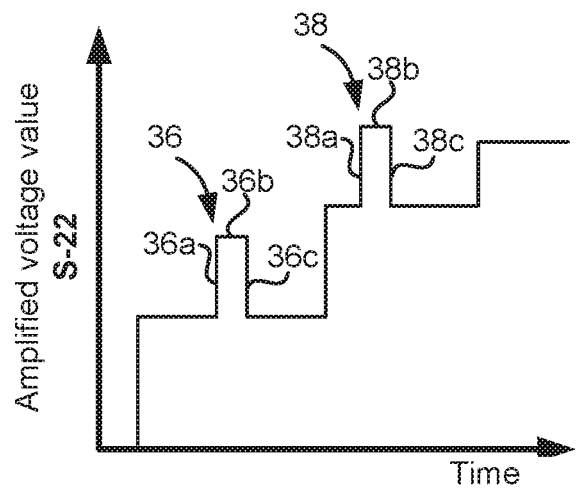
FIG. 3A is an exemplary graph of amplified voltage value with simultaneous calibration pulse injection according to the present disclosure.
Figure 3B:
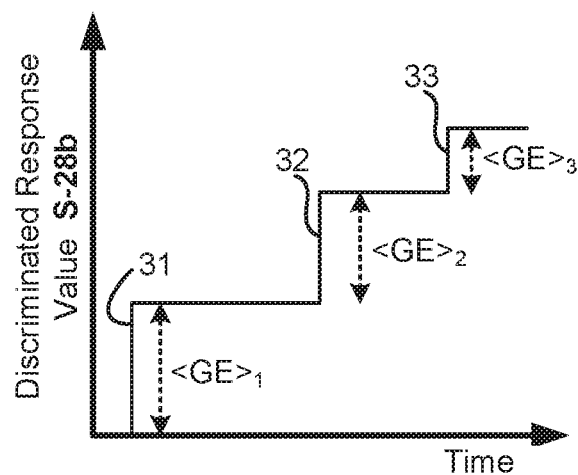
FIG. 3B is an exemplary graph of discriminated signal value with simultaneous calibration pulse injection according to the present disclosure.
Figure 3C:
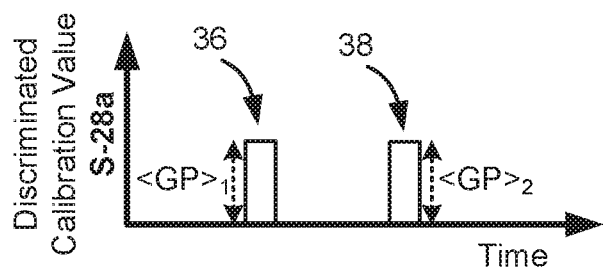
FIG. 3C is an exemplary graph of discriminated calibration value with simultaneous calibration pulse injection according to the present disclosure.

FIGS. 3A, 3B and 3C illustrate the operation of pulse discriminator 28. FIG. 3A shows a graph of amplified voltage value S-22, which includes a mixture of detector response and calibration values. In general, a detector response causes a rise in the value of amplified voltage value S-22, because detector 10 incorporates a charge sensitive pre-amplifier (not shown) in which charge from successive responses accumulates to cause rising voltage. On the other hand, calibration pulses originate from pulser 12 in which there is no charge sensitive amplifier, so that each calibration pulse causes an initial rise followed by a fall in the value of amplified voltage value S-22. FIG. 3A illustrates two calibration pulses, 36 and 38, with initial rising values 36a and 38a respectively, flat regions 36b and 38b respectively, and falling values 36c and 38c respectively. Pulse discriminator 28 may distinguish the calibration pulses by their falling values 36c and 38c which are not present in detector response values. Alternatively, pulse discriminator 28 may distinguish the calibration pulses using timing signals obtained from pulser 12 (not shown). Using either discrimination method, pulse discriminator 28 identifies calibration pulses 36 and 38, and removes them to produce discriminated response value S-28b as shown in FIG. 3B. Information from the removed calibration pulses is used to produce discriminated calibration value S-28a as shown in FIG. 3C.

FIG. 3B illustrates how the discriminated response value S-28b is used to derive an amplified energy signal for each X-ray incident on detector 10. The response to three incident X-rays can be identified in FIG. 3B by rising values 31, 32, and 33. The magnitude of rising values 31, 32, and 33 corresponds to the quantities $<GE>_1$, $<GE>_2$ and $<GE>_3$ respectively. These quantities are used by energy scale corrector 26, together with knowledge of gain value S-24 obtained from calibration ratio calculator 24, in order to assign corrected energy value S-26 to each of the three X-rays. The energy values of all incident X-rays are obtained in this way during the measurement, and counts are accumulated to obtain an energy spectrum.

FIG. 3C illustrates discriminated calibration value S-28a, showing calibration pulses 36 and 38. The amplitudes of pulses 36 and 38 correspond to the quantities $<GP>_1$ and $<GP>_2$ respectively. These quantities are used by calibration ratio calculator 24 together with reference pulse value S-16 to calculate gain value S-24. Different values of $<GP>_1$ and $<GP>_2$ may indicate that the overall gain $<G>$ of the electronic system has changed, and correction may automatically occur at energy scale corrector 26. Alternatively, rather than applying correction to gain $<G>$ at every successive calibration pulse, values of gain $<G>$ may be averaged over an averaging time which includes many pulses before applying a correction at energy scale corrector 26. Such averaging may be advantageous to reduce noise in the measurement of gain $<G>$ and is within the scope of the present disclosure.

Figure 4:
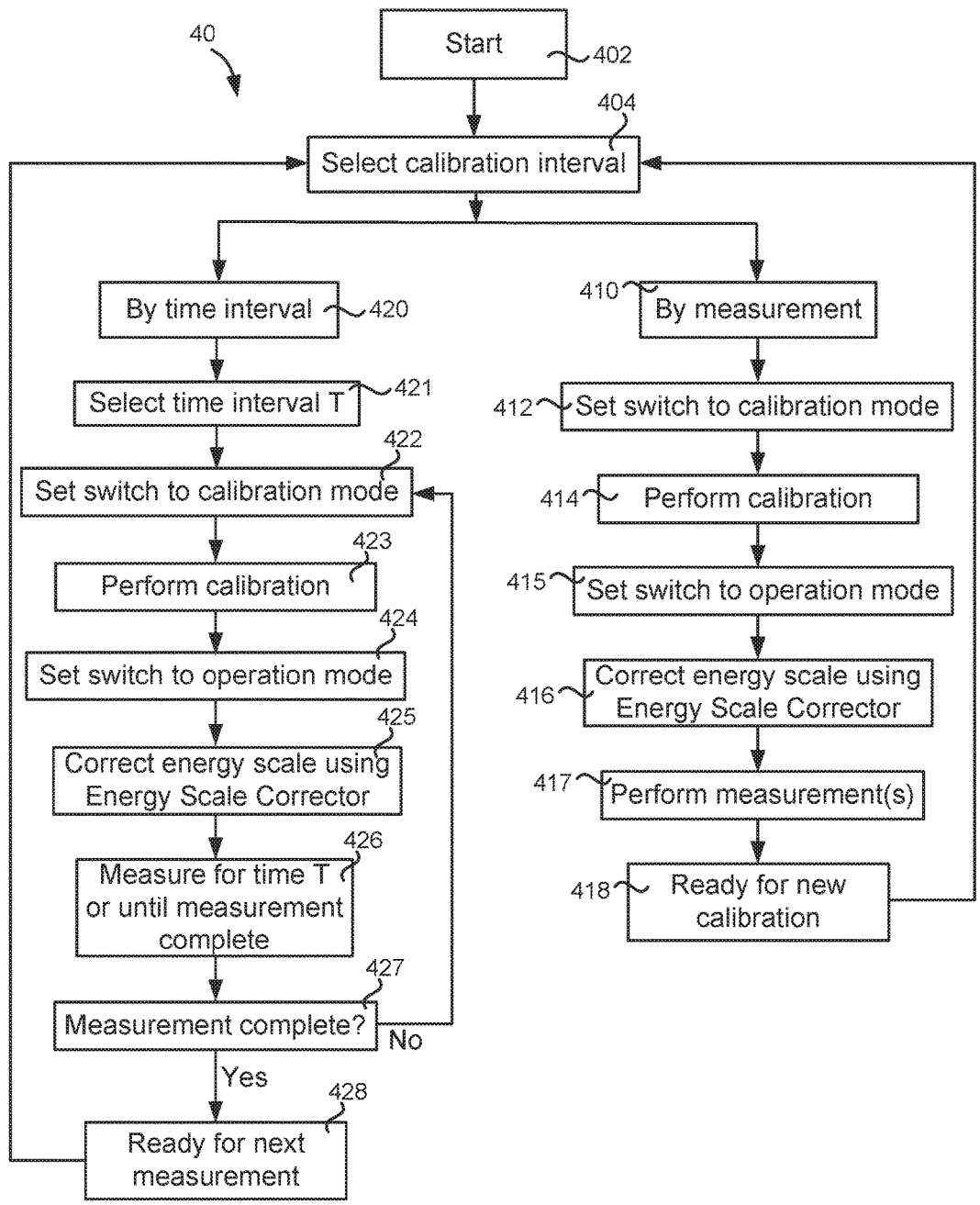
FIG. 4 is a schematic flow diagram of sequential calibration according to the present disclosure.

FIG. 4 shows a schematic flow diagram of a sequential calibration process 40 according to the present disclosure. Process 40 is described below with reference to FIG. 4 and FIG. 1. Process 40 starts at step 402, and at step 404 an operator selection is made via calibration mode controller 21 as to whether calibration is to be performed after one or more measurements, or after a specified interval of operating time. If calibration after one or more measurements is selected, process 40 moves to step 410. At step 412, calibration mode controller 21 sets switch 20 to calibration mode and in step 414 calibration is performed. Calibration of step 414 comprises calculation by calibration ratio calculator 24 of the calibration ratio, which may be averaged over many pulses. In a typical embodiment herein presented, the calibration pulse frequency may be 500 kHz, and the averaging time in step 414 may be 100 msec. In this embodiment gain value S-24 at the end of the calibration is an average value of about 50,000 pulses. Gain value S-24 is represented by the symbol $<G>$.

At step 415, calibration mode controller 21 sets switch 20 to operating mode and in step 416 the energy scale is corrected using the value of $<G>$ derived in step 414. In step 417 one or more measurements are performed with corrected energy scale, and upon completion of the specified number of measurements the system is ready for a new calibration at step 418, and the process returns to step 404.

If at step 404 calibration after a specified interval of operating time is selected, process 40 moves to step 420. At step 421 the operator, via calibration mode controller 21, selects a time interval T between successive calibrations. At step 422, calibration mode controller 21 sets switch 20 to calibration mode and in step 423 calibration is performed in the same manner as described above for step 414. At step 424, calibration mode controller 21 sets switch 20 to operating mode and in step 425 the energy scale is corrected using the value of $<G>$ derived in step 423. In step 426 the measurement is carried out until either clock 19 indicates that time T has expired or the measurement is complete, whichever occurs first. Step 427 tests whether the measurement is complete, and if not the process returns to step 422 for a new calibration. If measurement is complete, the process returns to step 404.

It can be seen that selection of calibration after a specified interval of operating time, as described in steps 420~428 allows one or more new calibrations to occur during the course of a single measurement. This may be useful for particularly long measurements. Setting of time interval T depends on the degree to which there is a stable environmental temperature—the less stable the environment the shorter time interval T should be set. In a typical embodiment, time interval T might be set to 10~100 seconds, and if calibration time is about 100 msec, there is no discernible interruption of instrument operation, even though calibration is occurring with sufficient frequency to avoid any risk of drift of the electronic gain.

It can be appreciated that, for both embodiments of calibration by time interval or by measurement operations, calibration switching can be initiated either by an automatic trigger or by manual triggering by the operator. All of such variations of implementation are within the scope of the present disclosure.

Figure 5:
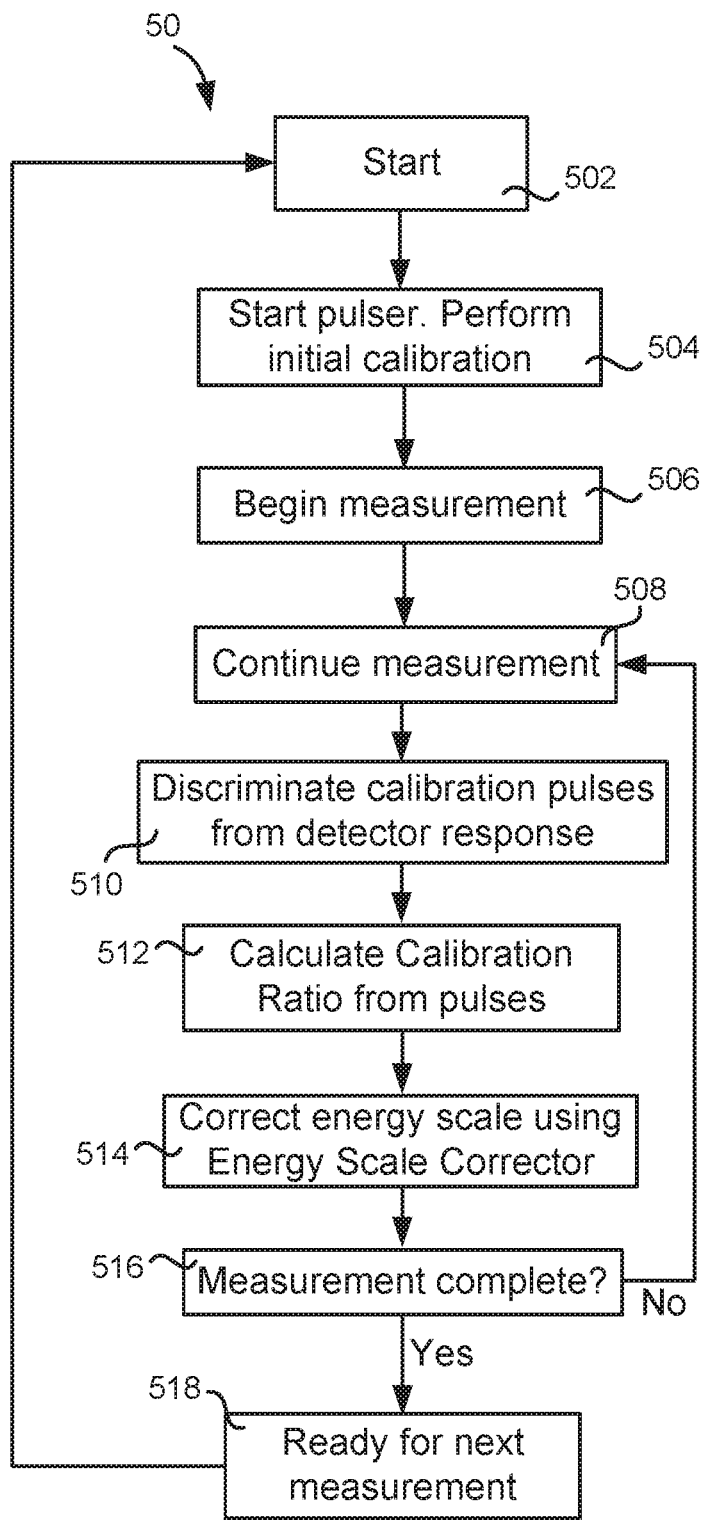
FIG. 5 is a schematic flow diagram of simultaneous calibration according to the present disclosure.

FIG. 5 shows a schematic flow diagram of a simultaneous calibration process 50 according to the present disclosure. Process 50 is described below with reference to FIG. 5 and FIG. 2. Process 50 starts at step 502, and at step 504 pulser 12 is started in order to perform an initial calibration prior to beginning actual operation of the instrument. The initial calibration is performed for an initial calibration time which is sufficiently large to allow calibration ratio calculator 24 to calculate gain value S-24 by averaging over a large number of pulses. In an embodiment, the initial calibration time may be 100 msec to 1 second.

In step 506, the measurement is started by activating the X-ray source and directing X-rays at a sample. In step 508 the measurement is continuing, so that both detector response signal S-10 and calibration pulse signal S-12 are input into amplifier 18 and subsequently to processing ADC 22 and pulse discriminator 28. In step 510, pulse discriminator 28 separates calibration pulses and detector response into discriminated calibration value S-28a and discriminated response value S-28b respectively. In step 512 calibration ratio 24 is calculated and, after the averaging time, an updated gain value S-24, denoted by the symbol <G>, is provided to energy scale corrector 26. Energy scale corrector 26 updates the energy scale to its most recent updated value in step 514, using the value of <G> derived in step 512. In step 516 there is a check of whether the measurement is complete. If not, process 50 loops back to step 508 and the measurement continues uninterrupted.

It should be noted that the time taken from step 508 to step 516 is almost entirely due to the averaging time which, in an embodiment, is about 100 msec As a result, the energy calibration is updated every 100 msec throughout the measurement. In an embodiment, the pulse frequency of pulser 12 may be 50 kHz, which is 10 times lower than the pulse frequency used in process 40 as described in connection with FIG. 4. The reason for using a lower calibration pulse frequency in process 50 is that, since both calibration pulses and detector signals are processed simultaneously, there is a risk that a calibration pulse and detector signal are so closely coincident in time that neither may be distinguished. The probability of such close coincidence can be reduced by lowering the calibration pulse frequency. Nevertheless, at a frequency of 50 kHz, 5,000 pulses are averaged in 100 msec, which is sufficient to obtain reliable updated gain value S-24 for use during the next 100 msec measurement interval.

If the measurement is complete at step 516, the instrument is ready for the next measurement at step 518 and the process loops back to the start at step 502.

It should be noted that the simultaneous calibration method of process 50 is particularly useful for measurements with low X-ray count rates. Such measurements are lengthy and frequent calibration is essential to ensure that gain drift during the course of the measurement is taken into account.

Figure 6:
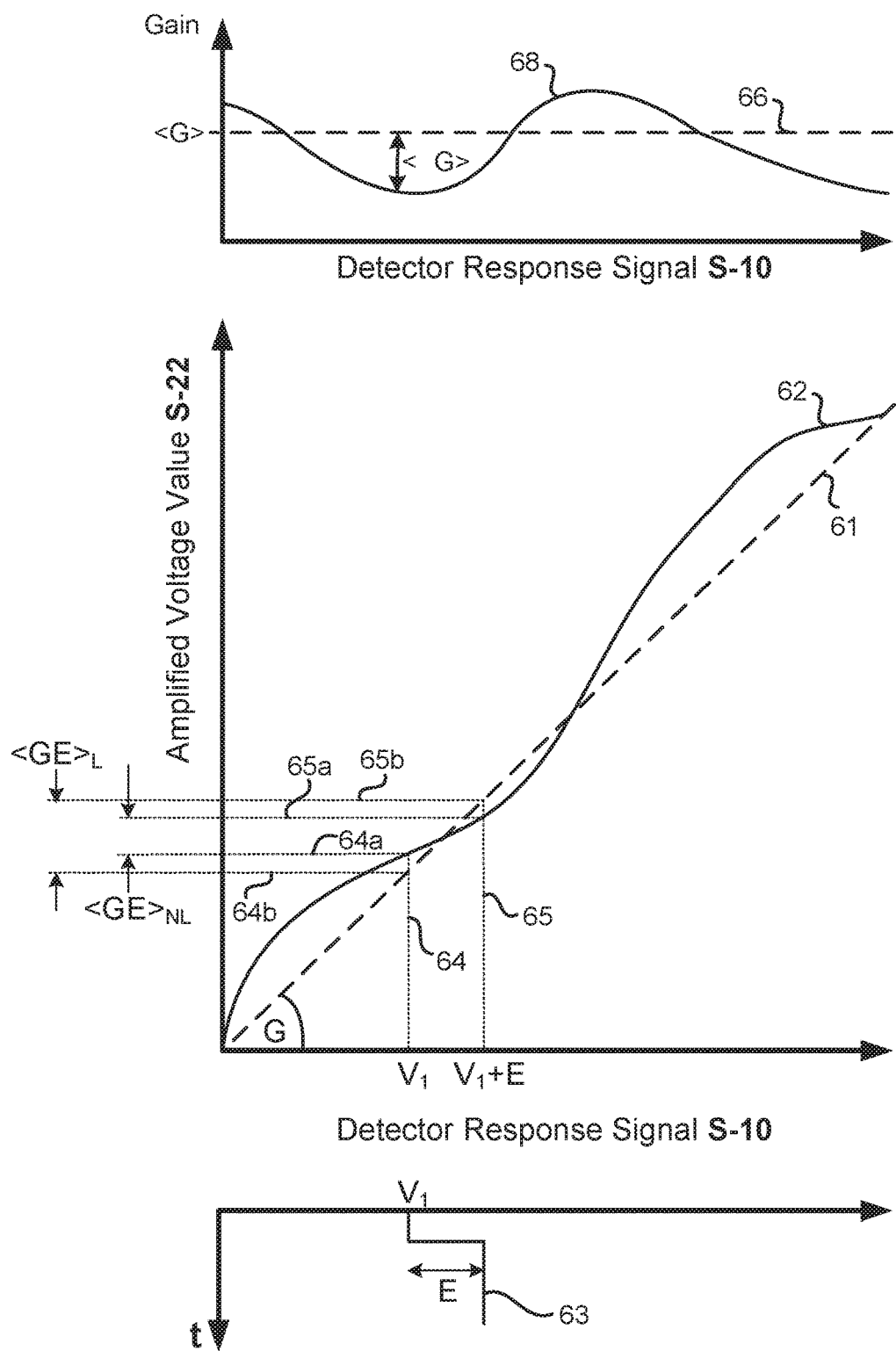
FIG. 6 shows graphs illustrating the effect of non-linearity on gain and amplified voltage value.

Circuits 1a and 1b in FIGS. 1 and 2 and processes 40 and 50 in FIGS. 4 and 5, as described above, all relate to calibration of the overall gain of the amplification and digitization electronics. However, no account is taken of non-linear effects. Referring now to FIG. 6, and with continued reference to FIG. 1, there are shown in FIG. 6 graphs illustrating the effect of non-linearity on an exemplary detector response signal 63, in which an X-ray arrives at detector 10 at a time when the charge-sensitive pre-amplifier voltage is $V_1$. The step-function increase in detector response signal S-10 is representative of the energy E of the X-ray.

On a graph of amplified voltage value S-22 vs detector response signal S-10, the voltages of detector response signal S-10 before and after arrival of the X-ray, $V_1$ and $V_1+E$ respectively, are shown by lines 64 and 65 respectively. A line 61 shows the behavior of a perfectly linear amplification and digitization electronic system, wherein the gain G is equal to the slope of the line as shown. However, if the gain is not linear, then the actual gain is represented by the slope of a line 62, and although the slope of line 61 is the average of the slope of line 62, the slope at any particular point on line 62 may be different from the slope of line 61, and therefore the gain may be different.

In a graph of gain vs detector response signal S-10 shown at the top of FIG. 6, a line 66 is the slope of line 61 and represents the constant gain of a perfectly linear system, and a line 68 is the slope of line 62 and represents the varying gain of a non-linear system. Line 66 is the average value of line 68. The quantity <ΔG> represents the difference between the linear and non-linear gain, and it is to be understood that <ΔG> is a varying function of detector response signal S-10.

It should be noted that, in order to clearly illustrate the effect of the non-linearity, the deviation of line 62 from linear gain line 61 and of line 68 from line 66 has been greatly exaggerated relative to actual non-linearity of available electronic systems. Similarly, the size of step function E has been greatly exaggerated relative to the overall range of detector response signal S-10 and amplified voltage value S-22.

Lines 64 and 65, representing the change in detector response signal S-10 due to detector response signal 63, intersect line 61 at lines 64b and 65b respectively. Lines 64 and 65 intersect line 62 at lines 64a and 65a respectively. If the electronic system gain is linear, corresponding to line 61, then the change in amplified voltage value S-22 is given by the difference between the values of lines 65b and 64b, represented by the symbol $<GE>_L$. On the other hand, if the electronic system gain is non-linear, corresponding to line 62, then the change in amplified voltage value S-22 is given by the difference between the values of lines 65a and 64a, represented by the symbol $<GE>_{NL}$. It can be seen that $<GE>_{NL}$ is less than $<GE>_L$ and this is because the slope of line 62 is less than the slope of line 61 in the relevant part of the graph. However, if output voltage $V_1$ is different, the slopes of lines 61 and 62 may be different, and in some circumstances $<GE>_{NL}$ may be greater than $<GE>_L$.

Figure 7:
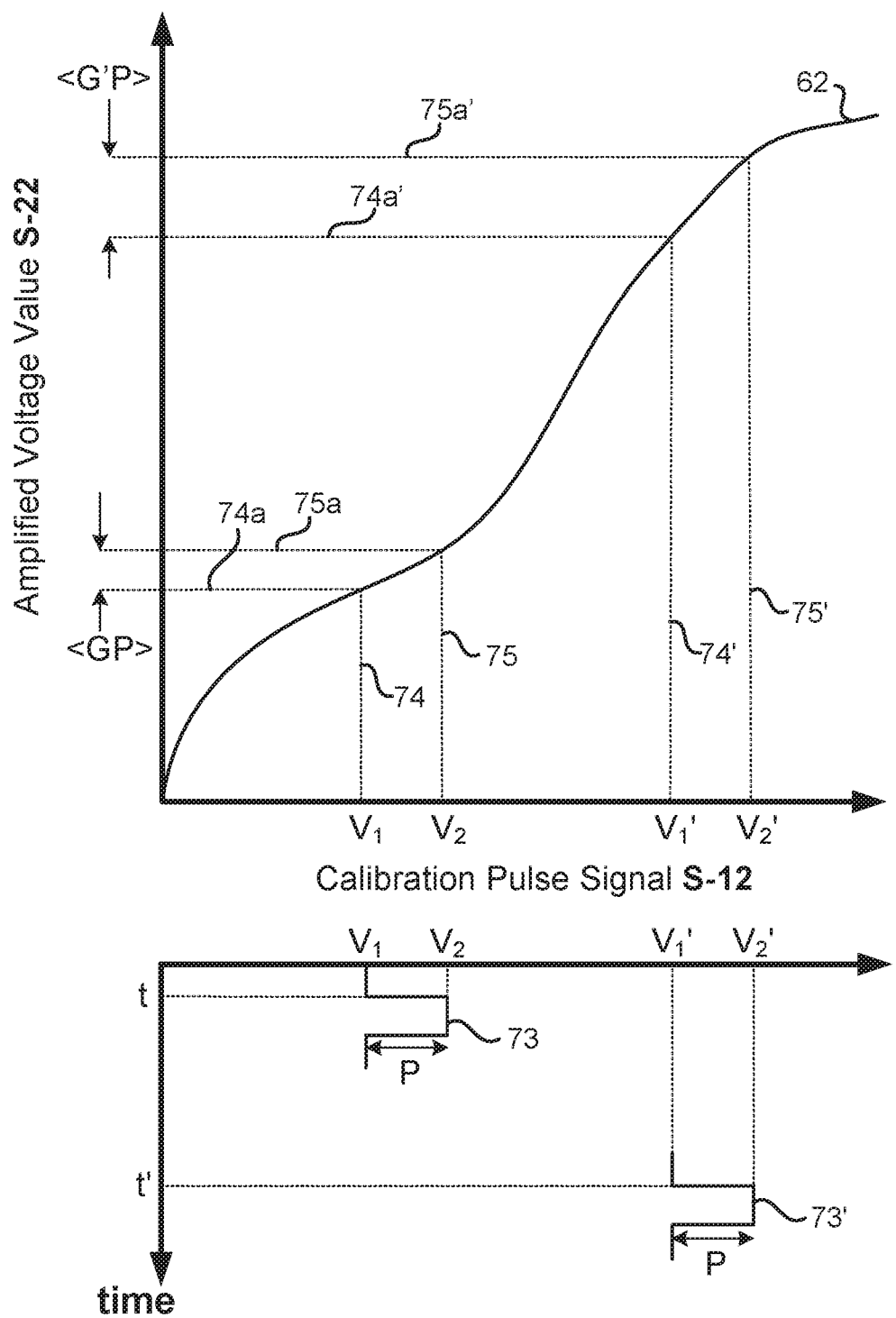
FIG. 7 shows graphs illustrating the use of calibration pulse signals for calibration of non-linearity effects according to the present disclosure.

FIG. 7 is a diagram illustrating a solution by use of calibration pulse signals for calibration of non-linearity effects. In order to calibrate for non-linearity effects, pulses are injected into the amplification and digitization system using a circuit 1c which is described below in connection with FIG. 8. In a graph of calibration pulse signal S-12 vs amplified voltage value S-22 shown in FIG. 7, non-linear response line 62 is the same as in the graph of detector response signal S-10 vs amplified voltage value S-22 as shown in FIG. 6. This is because calibration pulses and detector response signals are injected into the same amplification and digitization system, and therefore non-linear gain effects are unchanged.

FIG. 7 shows two exemplary calibration pulses, 73 and 73', which are injected into the amplification and digitization system at different times, t and t' respectively. Pulses 73 and 73' have, respectively, lower pulse voltages $V_1$, $V_1'$ and upper pulse voltages $V_2$, $V_2'$. Pulses 73 and 73' have the same pulse height P, meaning that $V_2-V_1=V_2'-V_1'=P$. Lower voltages $V_1$, $V_1'$ and upper voltages $V_2$, $V_2'$ are represented, respectively, by lines 74, 74' and 75, 75' on the graph of calibration pulse signal S-12 vs amplified voltage value S-22. Lines 74 and 75 intersect line 62 at lines 74a and 75a respectively, and the change in amplified voltage value S-22 due to pulse 73 is the difference between the values at lines 74a and 75a, represented by the symbol <GP>. Lines 74' and 75' intersect line 62 at lines 74a' and 75a' respectively, and the change in amplified voltage value S-22 due to pulse 73' is the difference between the values at lines 74a' and 74b', represented by the symbol <G'P>. It should be noted that G is the gain of the amplification and digitization system at the voltages $V_1$ and $V_2$ of pulse 73, and G' is the gain of the amplification and digitization system at the voltages $V_1'$ and $V_2'$ of pulse 73', and that G and G' are different due to non-linearity of the system. Note also that, in practice, pulse height P is very small relative to the overall range of detector response signal S-10 and amplified voltage value S-22. It can therefore be assumed that line 62 is linear over such a small range, and therefore there is no change of gain between voltages $V_1$ and $V_2$ or between voltages $V_1'$ and $V_2'$.

Figure 8:
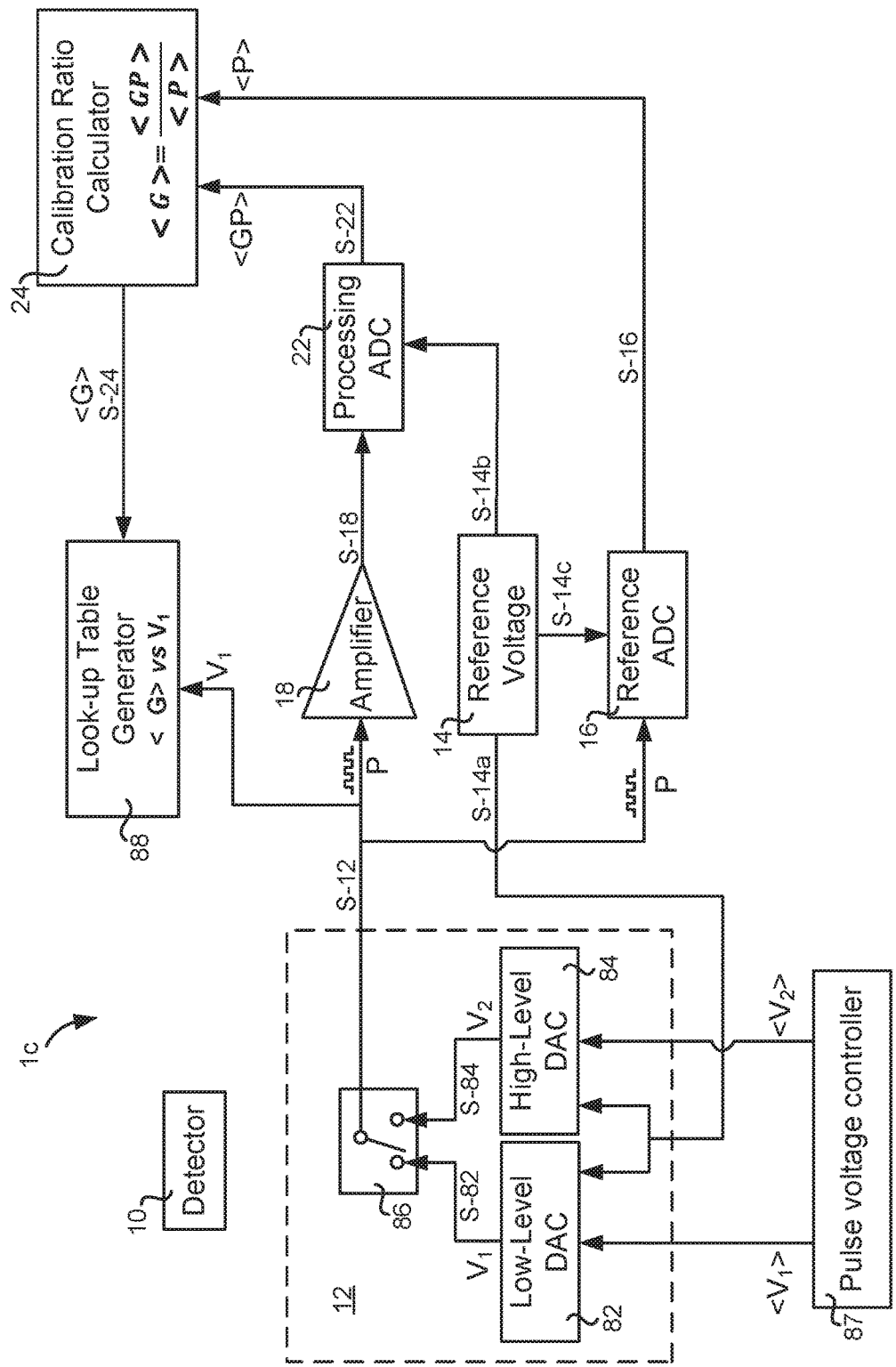
FIG. 8 is a schematic diagram of a circuit for calibration of non-linearity according to the present disclosure.

FIG. 8 is a schematic illustration of a circuit 1c, which is an alternative embodiment of circuit 1a shown in FIG. 1, and which is used to perform a one-time calibration of non-linearity during a manufacturing calibration phase. This calibration of non-linearity deals with the intrinsic non-linearity exhibited by both amplifier 18 and ADC 22, and is done only once at the manufacturing level.

It should be also noted that the description in FIGS. 6-10 of calibration for non-linearity is an improved calibration process which is independent of the on-board instrument gain calibration described in relation to FIGS. 1-5. The result of the non-linearity calibration is preferably a look-up table (described below) which is specific to each instrument, and that can be used by each specific instrument throughout its life.

FIG. 8 shows that pulser 12, which is the same pulser as that shown in FIGS. 1 and 2, comprises a low-level digital-to-analog converter (DAC) 82, a high-level DAC 84, and a pulser switch 86. A pulse voltage controller 87 produces a lower pulse voltage value <$V_1$> and a higher pulse voltage value <$V_2$>. Lower pulse voltage value <$V_1$> is input to low-level DAC 82, and, using reference voltage 14 as its reference via signal S-14a, DAC 82 produces a lower pulse voltage $V_1$ at signal S-82. Higher pulse voltage value <$V_2$> is input to high-level DAC 84, and, using reference voltage 14 as its reference via signal S-14a, DAC 84 produces a higher pulse voltage $V_2$ at signal S-84. Signals S-82 and S-84 are input to pulser switch 86 which operates at an operator defined frequency to switch its output between signals S-82 and S-84 thereby producing pulses with lower pulse voltage $V_1$ and higher pulse voltage $V_2$ at signal S-12.

Signal S-12 is the same as calibration pulse signal S-12 which was discussed in relation to circuit 1a in FIG. 1 and circuit 1b in FIG. 2. The remainder of circuit 1c is operates in the same way as circuits 1a and 1b, namely calibration pulse signal S-12 is input into amplifier 18 and processing ADC 22, and calibration pulse signal S-12 is also input into reference ADC 16. A calibration ratio is calculated by calibration ratio calculator 24 and after an averaging time, gain value S-24 is output, represented by symbol <G>, which is the gain corresponding to lower pulse voltage $V_1$ and higher pulse voltage $V_2$. Gain value S-24 and the value of $V_1$ are input to a look-up table generator 88. As explained below in connection with FIG. 9, pulse voltage controller 87 then changes the value of lower pulse voltage $V_1$, and calibration ratio calculator 24 computes a new gain value S-24 which may be different from the previous value due to non-linearity of the electronic gain. The new values of $V_1$ and gain value S-24 are input to look-up table generator 88. In this way, by changing values of $V_1$ and computing corresponding values of gain value S-24, look-up table generator 88 may build up a table of gain value S-24 and corresponding values of $V_1$ which covers the complete range of amplified voltage value S-22 and which contains as many calibration points as desired. When data acquisition for the desired calibration points has been completed, look-up table generator 88 computes an average gain value for all the calibration points, and converts the table to be a table of the difference, <ΔG>, between the gain value for each calibration point and the average gain value. Therefore, the final product of look-up table generator 88 is a table comprising multiple values of <ΔG> and corresponding values of $V_1$.

It should be noted that circuit 1c is equivalent to circuit 1a with switch 20 set to calibration mode and with addition of pulse voltage controller 87 and look-up table generator 88. Circuit 1c is also equivalent to circuit 1b with omission of detector response signal S-10 and addition of pulse voltage controller 87 and look-up table generator 88. Therefore, by adding pulse voltage controller 87 and look-up table generator 88, circuit 1c is available to perform calibration of non-linearity irrespective of whether an X-ray instrument is configured with circuit 1a or with circuit 1b. Note that detector 10 is present in FIG. 8, but is not operative during the calibration of non-linearity.

Figure 9:
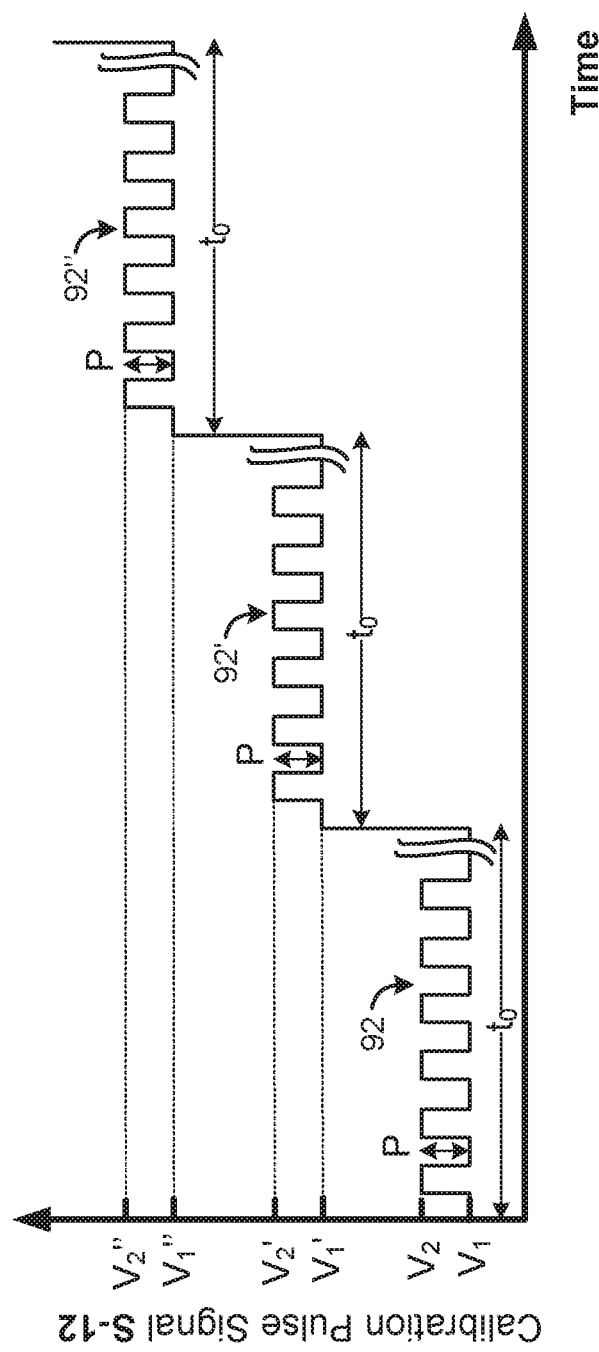
FIG. 9 is a graph showing exemplary pulse sequences for non-linearity calibration.

FIG. 9 shows an embodiment of calibration pulse signal S-12, which is a series of pulse sequences produced by pulse voltage controller 87 and pulser 12 for use in calibration of non-linearity. A pulse sequence 92 comprises pulses continuing for a calibration time $t_0$, with lower pulse voltage $V_1$, higher pulse voltage $V_2$ and pulse height P. When pulse sequence 92 is used in circuit 1c, calibration ratio calculator 24 averages the calibration ratio for time $t_0$ to produce a gain value S-24, representative of <G> at lower pulse voltage $V_1$. In an embodiment, calibration time to is 100 msec and the pulse frequency is 50 kHz, so that pulse sequence 92 comprises 5,000 pulses. Pulse sequence 92 is followed by a pulse sequence 92' which comprises pulses continuing for a calibration time $t_0$, with lower pulse voltage $V_1'$, higher pulse voltage $V_2'$ and pulse height P. When pulse sequence 92' is used in circuit 1c, calibration ratio calculator 24 averages the calibration ratio for time $t_0$ to produce a gain value S-24, representative of <G'> at lower pulse voltage $V_1'$. Pulse sequence 92' is followed by a pulse sequence 92" which comprises pulses continuing for a calibration time $t_0$, with lower pulse voltage $V_1"$, higher pulse voltage $V_2"$ and pulse height P. When pulse sequence 92" is used in circuit 1c, calibration ratio calculator 24 averages the calibration ratio for time $t_0$ to produce a gain value S-24, representative of <G"> at lower pulse voltage $V_1"$. Gain values <G>, <G'> and <G"> are measurements of gain at different lower pulse voltage $V_1$, $V_1'$ and $V_1"$ respectively, and these gain measurements therefore take into account the non-linearity of gain with respect to input voltage.

Gain values <G>, <G'> and <G"> and corresponding lower pulse voltage values <$V_1$>, <$V_1'$> and <$V_1"$> are input to look-up table generator 88 as shown in FIG. 8. Only three different lower voltages and corresponding gain values are shown in FIG. 9, but the number of corresponding lower voltages and gain values which can be obtained according to the invention is unlimited. By continuing to vary the lower pulse voltage in small increments over the full range of expected variation of detector response signal S-10, a calibration map is made of the non-linear gain characteristics of the amplification and digitization system. In effect, the calibration reproduces lines 62 and 68 as shown in FIGS. 6 and 7 over the full range of the instrument.

In subsequent operation of the instrument with input from detector response signal S-10, the non-linearity due to differing output levels of the charge-sensitive pre-amplifier is taken into account by energy scale corrector 26 using the table from table generator 88. Referring to FIGS. 1 and 2, it can be seen that gain value S-24, represented by symbol <G>, is not subject to non-linear variation because the lower pulse voltage of pulses from pulser 12 does not vary. However, the amplified voltage value S-22, represented by symbol <GE> is subject to non-linear variation depending on the output voltage of the charge sensitive pre-amplifier associated with detector 10. Energy scale corrector therefore corrects the energy <E> of an X-ray using the following modification of equation (2):

$$\langle E \rangle = \frac{\langle (G + \Delta G)E \rangle}{\langle G \rangle} \qquad (3)$$

where ΔG is derived from the table in table generator 88 according to the voltage $V_1$ of the charge sensitive preamplifier at the time the X-ray was received.

Figure 10:
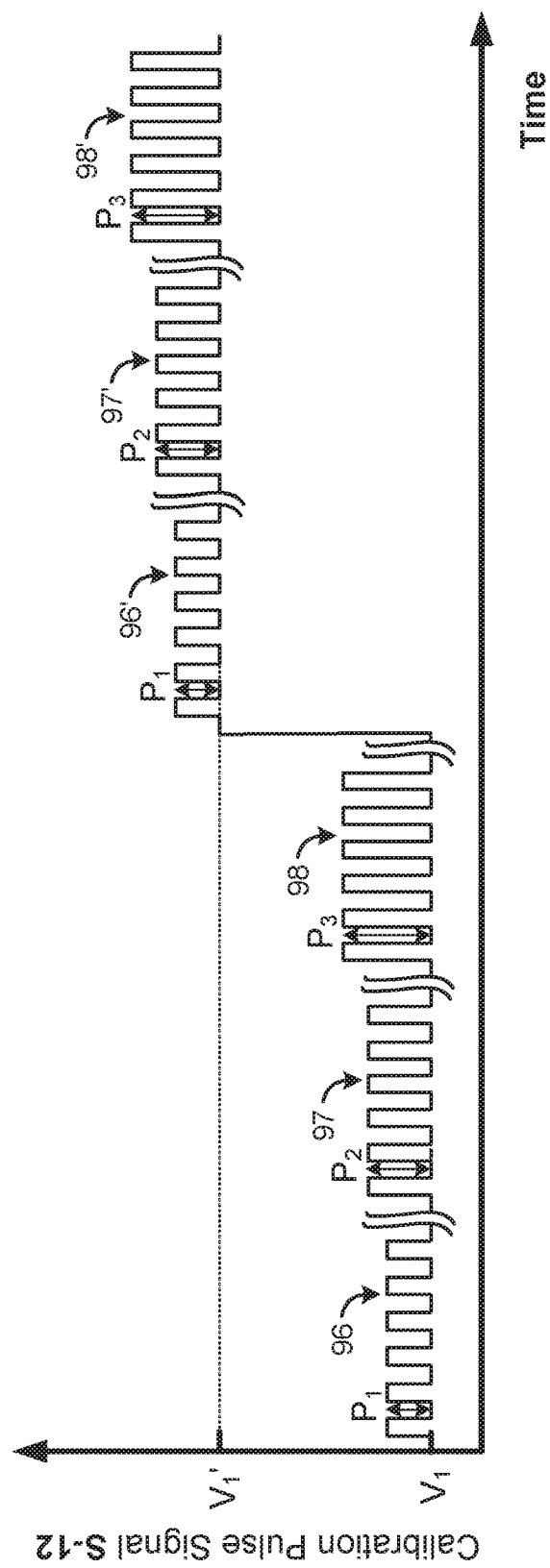
FIG. 10 is a graph showing alternative exemplary pulse sequences for non-linearity calibration.

Pulse height P is kept constant in pulse sequences 92, 92' and 92" shown in FIG. 9. However, as well as depending on the lower pulse voltage, the non-linear gain of the amplification and digitization system may also depend on the pulse height. FIG. 10 shows an alternative embodiment of calibration pulse signal S-12, which comprises pulse sequences 96, 97 and 98, all with the same lower pulse voltage $V_1$, but with differing pulse heights $P_1$, $P_2$ and $P_3$ respectively. In an embodiment, $P_1$ may represent a pulse height near the bottom of the voltage range of expected detector response signal S-10, $P_3$ may represent a pulse height near the top of the voltage range of expected detector response signal S-10, and $P_2$ may represent a pulse height at approximately midrange. Pulse sequences 96, 97 and 98 are followed by pulse sequences 96', 97' and 98', all with the same lower pulse voltage $V_1'$, and with pulse heights $P_1$, $P_2$ and $P_3$ respectively. In the same way as described in connection with FIG. 9, by continuing to vary the lower pulse voltage in small increments over the full range of expected variation of detector response signal S-10, a calibration map is made of the non-linear gain characteristics of the amplification and digitization system. However, for the pulse sequences of FIG. 10, for each value of lower pulse voltage there are three values of gain, one for each of low pulse height, mid pulse height and high pulse height. In effect, the calibration produces three version of lines 62 and 68 as shown in FIGS. 6 and 7 over the full range of the instrument, and the correct calibration for any pulse height may be determined by extrapolation between the measured calibration data for low-, mid- and high pulse height. In subsequent operation of the instrument with input from detector response signal S-10, non-linearity both due to differing output levels of the charge-sensitive pre-amplifier and due to differing X-ray energy are taken into account.

It should be noted that because the non-linearity has weak dependence on temperature, only a one-time calibration of the instrument non-linearity is required. This calibration may be conveniently performed in the factory before shipment of the instrument to a customer. On the other hand, the actual gain of the instrument is subject to drift, and it is necessary to apply the gain calibration methods described herein in connection with FIGS. 1~5. Referring to FIG. 6, the gain calibration methods of FIGS. 1~5 are designed to correct the slope of line 61 or the level of line 66, whereas the non-linearity calibration described in connection with FIGS. 6~10 is a determination of the deviation of line 62 from line 61 or, equivalently, the deviation <ΔG> of line 68 from line 66. It can be assumed with good accuracy that the deviation of line 62 from line 61 remains constant even as the slope of line 61 changes. When gain drift occurs during operation, line 62 pivots about the origin of the graph as the gain changes, but its shape does not change. Similarly, it can be assumed with good accuracy that the deviation of line 68 from line 66 remains constant even as the level of line 66 changes. When gain drift occurs during operation, line 66 moves up and down the graph as the gain changes, but its shape does not change.

The ability to calibrate the non-linearity of an amplification and digitization circuit as described in connection with FIGS. 6~10 is an important novel aspect of the present invention.

A further novel aspect is the combination of non-linearity calibration with automatic calibration of the system gain as described in connection with FIGS. 4 and 5.

Yet a further novel aspect is use of single common reference voltage 14 as voltage reference for processing ADC 22, for reference ADC 16 and for both low-level DAC 82 and high-level DAC 84.

Although the present invention has been described in relation to particular embodiments thereof, it can be appreciated that various designs can be conceived based on the teachings of the present disclosure, and all are within the scope of the present disclosure.

What is claimed is:

1. A detector signal processing circuit for a detector, the detector is used for detecting a fluorescence X-ray energy response in an X-ray analytical instrument and sending detector response signals, the instrument is configured to include an operating mode and a calibration mode, the instrument is further configured to accumulate the detector response signals and to compute an energy spectrum having an energy scale, the circuit comprises:

a pulse generating pulser providing calibration pulses with a pulsing amplitude and a pulser frequency, a single common reference voltage providing a reference voltage signal, a reference analog to digital converter (ADC) converting calibration pulses to a reference pulse value, at least one amplifier for amplifying an amplifier input, wherein the amplifier input is calibration pulses and/or the detector response signals and an amplifier output provides, respectively, an amplified pulse voltage and/or an amplified response signal voltage, a processing analog to digital converter (ADC) for providing a digitization process on the amplified pulse voltage and the amplified response signal voltage to produce a digitized pulse voltage value and a digitized response signal voltage value, respectively, a calibration ratio calculator calculating a calibration ratio of the pulse voltage value to the reference pulse value, and, an energy scale corrector calculating an operating mode ratio of the response signal voltage value to the calibration ratio, deriving a corrected energy scale based on the operating mode ratio, modifying the energy spectrum by applying the corrected energy scale to the energy spectrum, and outputting a corrected energy spectrum, wherein the single common reference voltage provides the reference voltage signal to the pulser, the reference ADC and the processing ADC.

2. The detector signal processing circuit of claim 1, wherein the calibration mode is associated with the amplifier input being the calibration pulses, and the operating mode is associated with the amplifier input being the detector response signals.

3. The detector signal processing circuit of claim 1, wherein the reference ADC is operational at a faster speed than the processing ADC.

4. The detector signal processing circuit of claim 1, wherein the reference ADC is a 24 bit ADC, and the processing ADC is a 16 bit ADC.

5. The detector signal processing circuit of claim 1, wherein the pulser is configured so that the pulsing amplitude is a typical amplitude of the detector response signals.

6. The detector signal processing circuit of claim 1, wherein the calibration ratio calculator is configured to calculate the calibration ratio based on an average ratio of the pulse voltage value to the reference pulse value for multiple successive pulses of the calibration pulses.

7. The detector signal processing circuit of claim 1, further comprising a switch switching the amplifier input to be either the calibration pulses or the detector response signals during the calibration mode and the operating mode, respectively.

8. The detector signal processing circuit of claim 1 wherein the amplifier input is a combined signal of the calibration pulses and the detector response signals.

9. The detector signal processing circuit of claim 8 further comprising a pulse discriminator discriminating the calibration pulses and separating the combined signal into separate signals of the calibration pulses and the detector response signals.

10. The detector signal processing circuit of claim 9, wherein the pulse discriminator is configured to discriminate the calibration pulses by at least one predetermined falling value indicative of calibration pulses.

11. The detector signal processing circuit of claim 9, wherein the pulse discriminator is configured to discriminate the calibration pulses by a predetermined frequency indicative of calibration pulses.

12. The detector signal processing circuit of claim 1, wherein the detector has a pre-amplifier voltage and the pulser further comprises a low level digital-to-analog converter (DAC) generating a lower pulse voltage, a high level DAC generating a higher pulse voltage, and a switch switching between the lower and the higher pulse voltages, and wherein the pulsing amplitude is equal to the difference between the higher and the lower pulse voltages.

13. The detector signal processing circuit of claim 1, wherein the detector has a pre-amplifier voltage and a pre-amplifier voltage range, including at least three pre-amplifier voltages substantially encompassing the pre-amplifier voltage range, and the pulser further comprises a low level digital-to-analog converter (DAC) generating a lower pulse voltage, a high level DAC generating a higher pulse voltage, and a switch switching between the lower and the higher pulse voltages, and wherein the pulsing amplitude is equal to the difference between the higher and the lower pulse voltages.

14. The detector signal processing circuit of claim 13, wherein the instrument is configured to include a non-linear calibration mode, wherein the pulser further includes a pulse voltage controller configured to generate pulses of the same pulsing amplitude and to control the lower pulse voltage to be sequentially at each of the pre-amplifier voltages.

15. The detector signal processing circuit of claim 14, further comprising a look-up table generator, coupled with an electronic memory, wherein the look-up table generator in the non-linear calibration mode generates a table having table values comprising values of the calibration ratio for corresponding values of the lower pulse voltage.

16. The detector signal processing circuit of claim 15, wherein the energy scale corrector in the operating mode is further configured to correct the response signal voltage value based on the table values for corresponding values of the pre-amplifier voltage.

17. A method of calibrating a detector signal processing circuit for processing detector response signals of a detector in an X-ray analytical instrument, the instrument configured to include an operating mode and a calibration mode, the instrument further configured to accumulate the detector response signals and to compute an energy spectrum having an energy scale, the circuit comprising a pulse generating pulser providing calibration pulses, a reference analog to digital converter (ADC) converting the calibration pulses to a reference pulse value, at least one amplifier having an amplifier input and an amplifier output, the amplifier output being input to a processing ADC having a processing ADC output, the method including the steps of:
 a) selecting that a calibration is performed after an N number of measurements;
 b) selecting the calibration mode wherein the calibration pulses are provided as the amplifier input, and wherein the processing ADC output is a digitized pulse voltage value;
 c) calculating a calibration ratio, wherein the calibration ratio is a ratio of the pulse voltage value to the reference pulse value;
 d) selecting the operating mode for the N number of measurements, wherein the detector response signals are provided as the amplifier input, and wherein the processing ADC output is a response signal voltage value;
 e) calculating an operating mode ratio, wherein the operating mode ratio is a ratio of the response signal voltage value to the calibration ratio;
 f) deriving a corrected energy scale based on the operating mode ratio and modifying the energy spectrum by applying the corrected energy scale to the energy spectrum thereby forming a corrected energy spectrum;
 g) outputting the corrected energy spectrum for each of the N number of measurements;
 h) selecting the calibration mode and calculating a new calibration ratio; and,
 i) returning to step d).

18. The method of claim 17 further including the steps of:
 a) selecting that the calibration is performed after a specified time interval;
 b) selecting the calibration mode and calculating the calibration ratio;
 c) selecting the operating mode, calculating the operating mode ratio and modifying the energy spectrum until the specified time interval has elapsed;
 d) selecting the calibration mode and calculating a new calibration ratio; and,
 e) returning to step c).

* * * * *